United States Patent [19]

Pum.

[11] 4,170,637
[45] Oct. 9, 1979

[54] FROSTING BLEACH COMPOSITION

[75] Inventor: Franz J. Pum, Canoga Park, Calif.

[73] Assignee: Redken Laboratories, Inc., Canoga Park, Calif.

[21] Appl. No.: 797,564

[22] Filed: May 16, 1977

[51] Int. Cl.$^2$ .............................................. A61K 7/135
[52] U.S. Cl. ........................................ 424/62; 8/110; 8/111; 252/186; 424/DIG. 3
[58] Field of Search ............... 424/DIG. 3, 62; 8/110, 8/111; 252/186

[56] References Cited

U.S. PATENT DOCUMENTS

| | | | |
|---|---|---|---|
| 3,193,464 | 7/1965 | Edman et al. | 424/62 |
| 3,378,444 | 4/1968 | Swanson | 424/62 |
| 3,726,967 | 4/1973 | Vorsatz et al. | 424/62 |
| 3,816,614 | 6/1974 | Zeffren et al. | 424/62 |
| 3,816,615 | 6/1974 | Zeffren et al. | 424/62 |
| 3,819,828 | 6/1974 | McCoy | 424/62 |
| 3,997,659 | 12/1976 | Knohl et al. | 424/62 |

*Primary Examiner*—James O. Thomas, Jr.
*Assistant Examiner*—Vera C. Clarke
*Attorney, Agent, or Firm*—Christie, Parker & Hale

[57] ABSTRACT

There is provided a composition for the frosting of hair comprised of an intimate mixture of particulate persulfate salts and alkaline silicates dispersed in an anhydrous organic carrier, the anhydrous organic carrier being sufficiently hydrophobic to retard absorption of atmospheric moisture and provided in a quantity sufficient to coat the particles to prevent persulfate decomposition in the presence of moist air. The carrier is sufficiently hydrophilic so as to be emulsifiable in an aqueous hydrogen peroxide solution to form with a thickener a viscous hair frosting emulsion.

9 Claims, No Drawings

FROSTING BLEACH COMPOSITION

BACKGROUND OF THE INVENTION

The present invention is directed to the frosting of hair. Hair frosting is the selective bleaching of strands of hair. Frosting bleaches are available in a powder form. The key ingredients are persulfate salts as the oxidant and alkali metal silicates present for pH control. The powdered bleaches include thickeners, surfactants, solid perfumes and the like, and are mixed with hydrogen peroxide solutions prior to use.

The persulfate salts are known to be unstable in the presence of atmospheric moisture and rapidly lose their active oxygen on exposure to humid air. Dusting during handling of the powder is yet another problem. Both the persulfates and the highly alkaline silicates are corrosive to equipment and, if inhaled, irritating to the mucus membranes and respiratory canals.

The present invention is directed to compositions which overcome the difficulties attendant to the use of dry oxidants for selective frosting of hair.

SUMMARY OF THE INVENTION

The disadvantages of the prior art of dry frosting bleaches are overcome by a composition comprising a mixture of at least one persulfate salt which is active towards the bleaching of hair and at least one alkali silicate, each in particulate form, in an amount of an anhydrous, organic carrier base provided in a quantity sufficient to coat the particles. An ingredient of the mixture is preferably at least one thickener. The organic base is sufficiently hydrophobic to protect against moisture absorption and sufficiently hydrophilic to enable a dispersion of the mixture in an aqueous hydrogen peroxide solution. The hydrophobic and hydrophilic properties may be provided through one or more compounds.

The resultant mixture in its pre-use state is stable against decomposition in the presence of atmospheric moisture even under conditions of high humidity, eliminate the problems of solids handling and is generally paste-like to a cream in consistency.

The composition is rendered active towards the selective bleaching of hair by addition of an aqueous hydrogen peroxide solution, such as a 6% or stronger hydrogen peroxide solution. In this combination provided thickeners form a cream of a viscosity suitable for selective application to strands of hair to be frosted.

In the mixture, the anhydrous organic carrier base is preferably present in an amount of from 30 to about 70% by weight, more preferably from about 40 to about 60% by weight, based on the total weight of the mixture.

Depending upon formulation of the mixture, a functional hair bleach is formed when the mixture is combined with an aqueous hydrogen peroxide solution in a quantity to yield a net cold (ambient temperature) emulsion having a pH of from about 8.2 to about 11.5, preferably from abut 9.8 to about 10.8. In the resultant aqueous emulsion, the provided persulfate serves as the oxidant for the bleaching process, while the alkali silicate provides the required pH. Usually, the weight ratio of the mixture to a 6% hydrogen peroxide solution will be from about 1:1 to about 1:4.

DETAILED DESCRIPTION

There is provided in accordance with the present invention, a mixture comprised of a mixture of particulate solid persulfate salts and particulate solid alkali silicates with a protective organic based carrier which is anhydrous in nature, but which includes ingredients which enables the resultant composition to form a dispersion or emulsion when mixed with an aqueous hydrogen peroxide solution.

The essential particulate ingredients in the mixture are the active persulfate salts such as ammonium persulfate, sodium persulfate, potassium persulfate and the like, as well as mixtures thereof, and at least one alkali silicate which will provide when the net emulsion is formed with an aqueous hydrogen peroxide solution, a bleaching composition in a desired pH range of from about 8.2 to about 11.5, perferably from about 9.8 to about 10.8. The alkali silicates which may be used include sodium silicate, sodium meta silicate, potassium silicate, potassium meta silicate, lithium silicate and the like. Other dry ingredients which may be present in particulate form include thickeners, surfactants, conditioners for the hair and the like.

The organic carrier base to which the dry particulate ingredients are added is anhydrous and comprised of compounds which are at least hydrophobic to the degree to render the net composition highly resistant towards absorption of moisture from the atmosphere and ingredients which are sufficiently hydrophilic to enable the composition to be dispersed or emulsified in an aqueous solution of hydrogen peroxide. In the organic carrier base, there may be included thickeners, surfactants, conditioners for the hair, as well as additives such as perfumes and the like.

Thickeners are essential to end use of the composition. Preferably, they are provided as a dry particulate component as a component of the organic carrier base or both. The less desirable alternate is to reserve them as a separate ingredient to be added when the aqueous bleach composition is formulated. If present in the mixture, the thickeners are normally latent, that is they do not, by necessity, serve to thicken the mixture, but are active upon addition of the mixture to an aqueous solution of hydrogen peroxide to render the net mixture sufficiently viscous as in the form of a cream or a paste to enable the bleach to be selectively applied to strands of hair so as to preclude carryover to adjacent strands of hair during normal treating operations.

Basic raw materials which are used for the formulation of the organic based carrier for the dry particulate solids include low volatility hydrocarbons such as mineral oil, petrolatum, high molecular aliphatic or alicyclic hydrocarbons such as polyethylene waxes and the like which are hydrophobic; hydrophobic waxes such as beeswax, synthetic spermacetti, glycerol monohydroxy stearate, microcrystalline waxes and the like; gums such as xanthan gum, alginates, guar gums and the like; branch chain fatty acid esters containing from about 10 to 18 carbon atoms such as isostearyl pentanoate; long chain alcohols containing from 8 to about 20 carbon atoms in the chain such as lauryl alcohol, oleyl alcohol, cetyl alcohol and the like; fatty acids containing from about 4 to about 22 carbon atoms in the chain, which acids may be saturated or unsaturated such as oleyl, lauryl, myristyl, cetyl, stearyl and the like; alcohols which may be aliphatic or alicyclic containing up to about 6 carbon atoms in the chain such as propanol, isopropanol, cyclohexanol and the like; glycols such as ethylene glycol and propylene glycol; polyethylene glycols; methoxylpolyethylene glycols; surfactants which may be anionic or non-ionic in nature, such as sodium lauryl sulfate, polyoxyethylene sorbitan esters, sorbitan esters, sodium sulfosuccinates, organic phosphate esters and the like; soaps; thickeners; perfumes; hair conditioning agents and the like.

Of the total ingredients, each must be anhydrous, at least one must be sufficiently hydrophobic in nature and present in an amount sufficient to substantially prevent takeup of moisture from the atmosphere.

For instance, the hydrocarbons are essentially hydrophobic. So too are most branch chain fatty esters. The fatty acid and fatty alcohols, depending upon the number of carbon atoms in the chain display varying degrees of hydrophobic character.

In the absence of a compound which is totally hydrophobic, the selection of such compounds for the composition must be to provide a net mixture which is sufficiently hydrophobic to substantially prevent acceptance of moisture from the air.

To enable dispersion in the aqueous hydrogen peroxide solution, there is present a mixture either in the organic based carrier a compound of sufficient hydrophilic nature to enable the mixture to be dispersed or emulsified in a hydrogen peroxide solution.

Another ingredient of functional bleach is a thickener. This ingredient may be externally provided, but is preferably part of the solids and/or the organic based carrier therefor. They include cellulosic compounds, both cationic and nonionic in nature as well as their derivatives.

The total of ingredients which form the organic carrier serve to completely coat the solid particles to prevent their contact with atmospheric moisture. To achieve this result, the organic based carrier is normally provided in an amount of from 30 to about 70% by weight, preferably from about 40 to about 60% by weight, based on the total weight of the mixture. Formulation is to occur under substantially anhydrous conditions.

As indicated, as additional ingredients to the net mixture, there may be provided conditioners for the hair which in the liquid state would not normally be available in the powder bleach, perfumes and the like. Other ingredients include chelating agents such as ethylenediaminetetracetic acid and salts thereof, which serve to sequester heavy metal compounds which may find their way into the mixture as well as colloidal silica which serves not only as a thickening agent but also as a scavenger to absorb trace amounts of free water which may be present in the compounds introduced in the formulation of the mixture.

While anhydrous and hydrophobic, at least to the degree of retarding during normal shelf life absoprtion of moisture from the atmosphere, the mixtures of this invention, by virtue of the hydrophilic groups present as by the simple presence of surfactants or soaps, are readily dispersible in aqueous solutions of hydrogen peroxide. The amount added is to provide a pH of from about 8.2 to about 11.5, preferably from about 9.8 to about 10.8.

Typically this is achieved in addition to the mixtures of this invention to a 6% hydrogen peroxide solution in a weight ratio of about 1:1 to about 1:4. The provided thickeners will form a net composition of a gel to a cream in consistency, but of sufficient fluidity for selective application to strands of hair.

The amount of each blended will, of course, vary on hydrogen peroxide strength. Hydrogen peroxide may be provided as a 6% solution, a 9% solution or a stronger solution. Hydrogen peroxide may also be provided as part of an aqueous based gel or cream.

In formulating the basic compositions of this invention, the solids may be blended separately from the organic based carrier, and the two combined from master batches of each or all ingredients added in one operation.

The formulated compositions of this invention exhibit unusually long shelf life in respect to retention of activity of the provided persulfates, low corrosion and irritation characteristics, and can, by the addition of hair conditioners and the like, provide in one composition a medium for improving the cosmetic conditioning and manageability of the hair by reducing hair damage during the bleaching operation which features would not be otherwise provided in a single composition.

In the following Examples, Examples 1 to 3 give formulations of useful particulate bleach formulations for blending in an anhydrous organic carrier. Examples 4 to 9 give formulations of an anhydrous emulsifiable organic carrier which, when blended with the compositions of Examples 1 to 3 in concentrations of from 30% to 70% by weight solids based on the weight of solids and the carrier, are moisture stable and emulsifiable when combined with aqueous solutions of hydrogen peroxide. Examples 10 to 13 give illustrative specific formulations of the moisture stable mixtures. Examples 14 to 15 give formulations for one step mixtures.

EXAMPLE 1

| Component | % by Weight |
|---|---|
| Ammonium persulfate | 60.00 |
| Potassium persulfate | 10.00 |
| Sodium meta silicate | 20.00 |
| Ivory soap | 9.00 |
| Trisodium salt of ethylenediaminetetracetic acid | 1.00 |
| | 100.00 |

EXAMPLE 2

| Component | % by Weight |
|---|---|
| Ammonium persulfate | 50.00 |
| Potassium persulfate | 10.50 |
| Sodium silicate | 25.00 |
| Carboxymethylcellulose | 2.00 |
| Soap flakes | 12.00 |
| Trisodium salt of ethylenediaminetetracetic acid | 0.50 |
| | 100.00 |

EXAMPLE 3

| Component | % by Weight |
|---|---|
| Ammonium persulfate | 40.00 |
| Potassium persulfate | 16.00 |
| Sodium meta silicate | 25.00 |
| Trisodium salt of ethylenediaminetetracetic acid | 0.50 |
| Ivory beads | 12.00 |
| Polymer JR-125 TM [a] | 6.00 |
| Powder Perfume | 0.50 |
| | 100.00 |

EXAMPLE 4

| Component | % by Weight |
| --- | --- |
| Mineral oil | 62.00 |
| Isostearyl pentanoate | 21.00 |
| Beeswax | 10.00 |
| Polymer JR-30M | 1.80 |
| Xanthan gum | 1.70 |
| Cab-O-Sil[b] M-5 TM | 3.50 |
| | 100.00 |

[b]A colloidal silica manufactured and sold by Cabot Corporation.

The beeswax was dissolved in the mixture of mineral oil and isostearyl pentanoate. To the mixture heated to 40° C., there was added the xanthan gum, Polymer JR-30M, and Cab-O-Sil M-5. After mixing to a homogeneous state, the mixture was allowed to cool until used.

EXAMPLE 5

| Component | % by Weight |
| --- | --- |
| Mineral oil | 55.00 |
| Isostearyl pentanoate | 28.00 |
| Synthetic beeswax | 10.00 |
| Carboxymethylcellulose | 3.50 |
| Cab-O-Sil M-5 | 3.50 |
| | 100.00 |

The mineral oil and isostearyl pentanoate were placed in a mixer and heated prior to adding the synthetic beeswax to aid solution. The carboxymethylcellulose and Cab-O-Sil M-5 were then added and the mixture stirred until homogeneously blended.

EXAMPLE 6

| Component | % by Weight |
| --- | --- |
| Mineral oil | 85.00 |
| Emulsifier, Tween 20 TM [c] | 11.00 |
| Cab-O-Sil M-5 | 4.00 |
| | 100.00 |

[c]A polyoxyethylene derivative of Sorbitan Monolaurate manufactured and sold by Atlas Chemical Industries, Inc.

The mineral oil and Tween 20 and add Cab-O-Sil were combined and mixed to form a uniform blend.

EXAMPLE 7

| Component | % by Weight |
| --- | --- |
| Brij TM 30[d] | 63.00 |
| Oleyl alcohol | 17.00 |
| Ethylene glycol MS | 7.00 |
| Ethylene glycol | 10.00 |
| Cab-O-Sil M-5 | 3.00 |
| | 100.00 |

[d]A polyoxyethylene ether of an aliphatic alcohol manufacture and sold by Ashland Chemical Company.

The above components were combined and mixed to a uniform consistency.

EXAMPLE 8

| Component | % by Weight |
| --- | --- |
| Polyethylene glycol (PEG) 6000 distearate | 40.00 |
| Adol TM 330[e] | 49.00 |
| Isopropanol | 11.00 |
| | 100.00 |

[e]A fatty alcohol manufactured and sold by Archer Daniels Midland Co.

Premelt PEG 6000 distearatre and with stirring add Adol 330 and isopropanol.

EXAMPLE 9

| Component | % by Weight |
| --- | --- |
| Brij 30 | 56.00 |
| Isopropanol | 25.00 |
| Isopropyl myristate | 3.00 |
| PEG 6000 monostearate | 6.00 |
| Carbowax TM 1500[f] | 6.00 |
| Klucel TM MF[g] | 4.00 |
| | 100.00 |

[f]A polyethylene glycol manufactured and sold by Union Carbide Corporation.
[g]A cellulose based thickener manufactured and sold by Hercules, Inc.

To a melt of PEG 6000 monostearate and Carbowax 1550, there was added Brij 30, isopropyl myristate and Klucel MF. After cooling, the isopropanol was added and the combination well blended.

EXAMPLE 10

An emulsifiable moisture resistant composition was prepared by slow blending of 60 parts by weight of the composition of Example 1 with 40 parts by weight of the composition of Example 5 until a uniform dispersion was obtained.

EXAMPLE 11

A uniform dispersion was obtained by slowly agitating 55 parts by weight of the composition of Example 4 while slowly adding 45 parts by weight the dry composition of Example 3.

EXAMPLE 12

As in Examples 10 and 11, the uniformly blended mixture was composed of 50 parts by weight of the composition of Example 2 and 50 parts by weight of the composition of Example 5.

EXAMPLE 13

As in Examples 10 and 11, a uniformly blended mixture was obtained by mixing 70 parts by weight of the composition of Example 3 and 30 parts by weight of the composition of Example 6.

EXAMPLE 14

| Component | % by Weight |
| --- | --- |
| Mineral oil | 31.00 |
| Isostearyl pentanoate | 10.50 |
| Synthetic beeswax | 5.00 |
| Polymer JR-30M | 3.90 |
| Xanthan gum | 0.75 |
| Cab-O-Sil M-5 | 1.75 |
| Ammonium persulfate | 20.00 |
| Potassium persulfate | 8.10 |
| Sodium metal silicate | 12.50 |
| Trisodium salt of ethylenediaminetetracetic acid | 0.25 |
| Ivory beads | 6.00 |
| Perfume | 0.25 |

| Component | % by Weight |
|---|---|
| | 100.00 |

The mineral oil and isostearyl pentanoate were mixed and heated to 45° C. The synthetic beeswax was dissolved in the heated mixture. Polymer JR-30M, xanthan gum and Cab-O-Sil M-5 were blended in and resultant mixture cooled. After cooling, the balance of the components were added with mixing until a uniform dispersion was obtained.

EXAMPLE 15

| Component | % by Weight |
|---|---|
| Mineral oil | 34.50 |
| Isostearyl pentanoate | 10.40 |
| Synthetic beeswax | 6.20 |
| Xanthan gum | 1.00 |
| Cab-O-Sil M-5 | 1.90 |
| Ammonium persulfate | 22.30 |
| Potassium persulfate | 8.30 |
| Sodium meta silicate | 12.90 |
| Trisodium salt of ethylenediaminetetracetic acid | 0.20 |
| Ivory beads | 2.30 |
| | 100.00 |

The synthetic beeswax was melted in a mixture of mineral oil and isostearyl pentanoate. The ivory beads, xanthan gum, and Cab-O-Sil M-5, were added and the mixture well blended and cooled to ambient temperature. Following this, the balance of the ingredients were added.

When the formulations of Examples 10 to 15 are mixed with 20 volume of hydrogen peroxide in varying proportions, a smooth bleaching cream was formed and applied to hair according to conventional methods for frosting.

What is claimed is:

1. A bleach composition for frosting of hair comprising an intimate mixture of at least one particulate persulfate salt and at least one particulate alkali silicate in an anhydrous organic carrier base provided in an amount sufficient to coat the particles present and form a mixture of paste to cream in consistency, the organic carrier base being sufficiently hydrophobic to substantially prevent absorption of atmospheric moisture by the mixture, and sufficiently hydrophilic to enable dispersion of the mixture in an aqueous solution of hydrogen peroxide.

2. A bleach composition for frosting of hair as claimed in claim 1 in which a thickener is present as part of the mixture.

3. A bleach composition as claimed in claim 1 in which the anhydrous organic carrier base is present in an amount of from about 30 to about 70% by weight based on the total weight of the mixture.

4. A bleach composition as claimed in claim 2 in which the anhydrous organic carrier base is present in an amount of from about 30 to about 70% by weight based on the total weight of the mixture.

5. A bleach composition as claimed in claim 1 in which the anhydrous organic carrier base is present in an amount of from about 40 to about 60% by weight based on the total weight of the mixture.

6. A bleach composition as claimed in claim 3 in which the anhydrous organic carrier base is present in an amount of from about 40 to about 60% by weight based on the total weight of the mixture.

7. A bleach composition for frosting of hair which comprises an intimate mixture of at least one particulate persulfate salt and at least one alkali silicate in an anhydrous organic carrier base which includes at least one substantially hydrophobic organic compound and at least one substantially hydrophilic organic compound, said organic base being present in an amount sufficient to coat the particles present and form a mixture of paste to cream in consistency, and sufficiently hydrophobic to substantially prevent absorption of atmospheric moisture by the mixture and sufficiently hydrophilic to enable dispersion of the mixture in an aqueous solution of hydrogen peroxide, said mixture including a thickener.

8. A bleach composition as claimed in claim 7 in which the anhydrous organic carrier base is present in an amount of from about 30 to about 70% by weight based on the total weight of the mixture.

9. A bleach composition as claimed in claim 7 in which the anhydrous organic carrier base is present in an amount of from about 40 to about 60% by weight based on the total weight of the mixture.

* * * * *